United States Patent [19]

Linkow

[11] Patent Number: 4,702,697
[45] Date of Patent: Oct. 27, 1987

[54] PREFABRICATED PARTIAL SUBPERIOSTEAL IMPLANT

[76] Inventor: Leonard I. Linkow, 1530 Palisades Ave., Fort Lee, N.J. 07024

[21] Appl. No.: 830,514

[22] Filed: Feb. 14, 1986

[51] Int. Cl.⁴ .............................................. A61C 8/00
[52] U.S. Cl. .................................... 433/173; 433/176
[58] Field of Search ........................ 433/173, 176, 189

[56] References Cited

U.S. PATENT DOCUMENTS 3,514,489  6/1970  Peterson ............................. 433/173

FOREIGN PATENT DOCUMENTS 2323210  1/1976  Fed. Rep. of Germany ...... 433/173

Primary Examiner—Robert Peshock
Attorney, Agent, or Firm—Darby & Darby

[57] ABSTRACT

A subperiosteal implant has a prefabricated elongated plate of pliable, work-hardenable material. A short projection extends from one surface of the plate and defines an aperture which receives a post for supporting an artificial tooth structure. The prefabricated implant is inserted through a lateral incision in the gum tissue, and is then molded to the bone. Subsequently the incision is sutured and the post is installed on the support plate.

6 Claims, 7 Drawing Figures

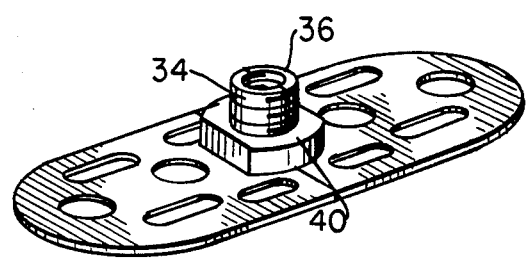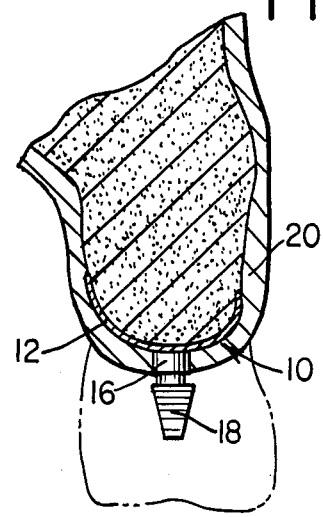

PREFABRICATED PARTIAL SUBPERIOSTEAL IMPLANT

TECHNICAL FIELD

This invention relates to supports for artificial dentures and, more particularly, to subperiosteal implants. One of the earlier techniques utilized by dentists to replace lost teeth involves fabricating and installing a removable bridge. In a typical removable bridge or denture, a resilient metal clasp is provided which is sprung around the adjacent natural teeth on either side of the edentulous span. A major difficulty with such removable bridges is that food particles tend to accumulate under the bridge and they require frequent removal to properly cleanse both the bridge and the gum areas. This is cumbersome and unpleasant. As a result, dentists often prefer to utilize the fixed or permanent bridge.

In installing a fixed bridge, the dentist grinds down the natural teeth adjacent to the edentuous span to form stubs. A support structure with artificial teeth is than snugly received over the natural tooth stubs, thereby permanently securing the entire bridge in place between the natural tooth stubs. However, often natural teeth do not remain on both sides of the edentuous span, or these natural teeth are so weak that they can not provide a reliable anchor for the end of the fixed bridge. To compensate for this, it has become quite common for the dentist to install implants which provide the support needed for a fixed bridge. These implants can generally be divided into the endosseous type and the subperiosteal type. The endosseous implant is generally described in U.S. Pat. Nos. 3,465,441 and 4,420,305, both of which issued to the present inventor. With an endosseous implant, a blade or a screw portion is surgically implanted in the bone of the of the alveolar ridge crest. A post projects from the implanted portion, and is used to support an artificial tooth or bridge.

Bone penetrating implants are excellent in many instances. However, the bone structure of a particular patient may not be very sturdy and disease may have caused resorbtion of the bone to such an extent that it is no longer sufficient to hold and receive the usual type of endosseous implant.

In situations where there has been a loss of bone to such an extent that an endosseous implant is contraindicated, dentists and oral surgeons have resorted to the subperiosteal implant. In this type of implant a metal plate is cast to fit over the exterior surface of the bone, but below the gum or periosteum. The formation of such a subperiosteal implant, however, is complex and requires several surgical procedures.

Previously, a two phase surgical procedure was utilized for installing a subperiosteal implant. During the first phase, an impression of the bone was taken. From this impression, an implant was designed and cast. A second procedure was preformed several weeks later to insert the implant which was fabricated from the impression taken during the first surgical procedure. During the first surgical procedure a long incision was made along most of the soft tissue covering the alveolar crest of the bone. This tissue was then reflected to expose enough of the bone to make an adequate impression. In the typical process, actually two impressions are made. The first impression is made with heavy silicone which is placed over the exposed bone. This silicone is then used to form a plaster model of the bone. A plastic tray is molded over or stamped to the model. Next the plastic model is covered with a rubber impression material and is fitted over the exposed bone of the patient. This rubber impression material forms the final impression.

While the rubber impression in its special fabricated tray remains over the bone, a standard full mouth tray with rubber-based impression model is placed into the patients mouth. When it hardens and is removed, it includes the rubber-based impression of the bone, as well as an impression of the remaining teeth in the patient's mouth. Using the impression, a master stone model is poured. When it has hardened it is used to form a duplicate investment model. A waxed version of the desired design of the subperiosteal implant is then made by a technician directly over the duplicate investment model. The protruding post of the wax model of the implant is made parallel to the remaining teeth, which are duplicated on the model.

The wax model is then surrounded by an investment molding material and used to form a mold by the lost wax molding technique. In this technique the mold is placed in an oven at 2150 F. to 2200 F. for two hours. Then a cobalt-chrome (Vitallium) casting of the implant is made and is allowed to cool down at least 30 minutes. The casting is then polished, washed and sterilized, which takes another 1 to 1 ½ hours.

Many hours of laboratory work have to be devoted in order to complete this casting. In addition, there is a significant amount of surgical time involved for the patient as well as the dentist. Further, the surgery for forming the implant and the second surgery for inserting it are usually done about three weeks apart so the patient is without dentures for a period of time. These surgeries require extensive reflecting of gum tissue and consequently cause great trauma. At the end of each surgery, many sutures are needed to close the long incision that is necessary both times. The second surgery is particularly difficult because it requires the surgeon to expose enough of the bone to allow for proper insertion of the implant, while still giving enough elasticity to the tissues to enable the sutures to close completely those tissues that are being stretched over a framework of metal that rests on top of the bone. Thus, it can be seen that, while the prior technique has a useful place in oral surgery, it is generally time consuming, traumatic, painful and costly to the patient.

DISCLOSURE OF INVENTION

The present invention is directed to overcoming the difficulties of subperiosteal implants by eliminating the need to especially cast an implant from a mold of the patient's bone structure. Instead a prefabricated subperiosteal implant is utilized.

In an illustrative embodiment of the invention, the implant is comprised of a flat plate of pliable metal material, i.g., Titanium. Extending from one surface of the plate is a small internally threaded collar for receiving a post which is intended to support an artificial tooth structure. In order to insert this implant, a buccolingual incision is made in the gum tissue at the center of the edentulous span. Then a tunneling procedure is used to separate the tissue from the alveolar ridge crest in both directions from the incision. This is done without an additional incision through the tissue and without reflecting the tissue. After the tissue has been separated from the bone, the flat plate is slid completely underneath the tissue distal to the incision so that the front end of the flat plate is at the bucco-lingual incision.

Then it is slid forward or anterior to the incision underneath the tissues until the internally threaded collar is positioned at the incision site. Then blunt dental instruments are used to bend and shape the Titanium plate to the bone under the gum tissue. This shaping of the plate tends to work harden the metal so that it assumes a relatively rigid structure.

Once the metal plate has been formed over the alveolar ridge crest of the bone, and is in close conformity therewith, the incision may be sutured such that it closely surrounds the protruding collar or may even be sutured over the collar so that the implant is completely out of operation. A period of time is then allowed to pass, during which the gum tissue re-establishes itself and firmly holds the implant in place. At this point, a small incision can be made to expose the collar. Then the post and an artificial tooth structure may be installed.

In one embodiment of the invention, the implant is formed in two halves, divided through the threaded collar. When the tissue has been tunneled to both sides of the incision, one half is slipped under the tissue in one direction, and the other half is slipped under the tissue in the other direction. The two halves are then brought together. In this version, the collar may have external threads such that the two halves may be fastened together by a cap which screws over the exterior threads.

Once sufficient time has passed for the implant portions to be firmly held in place, a coping for an artificial tooth structure is fabricated. This coping may be screwed over the outer threads which are provided in the protruding collar and acts as the posterior crown of a fixed prosthesis.

As an alternative the cap may be provided with an aperture that exposes the inner threads of the collar. In such a case the collar remains in place and the post is merely screwed through the aperture in the cap.

BRIEF DESCRIPTION OF THE DRAWINGS

The foregoing and other features of the present invention will be more readily apparent from the following detailed description and drawings of illustrative embodiments of the invention in which:

FIG. 6 is a perspective view of a two-piece subperiosteal implant held together by a threaded cap with an aperture; and FIG. 7 is a cross-sectional view through the implant of FIG. 1 along lines 7—7.

BEST MODE FOR CARRYING OUT THE INVENTION

Figure 1:
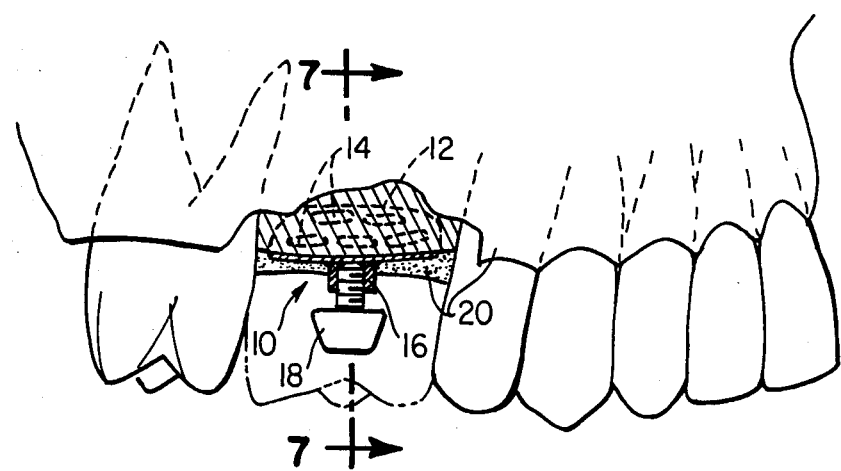
FIG. 1 is a side view of a patient's upper jaw showing a subperiosteal implant, according to the present invention, installed therein.

In FIG. 1 there is shown a subperiosteal implant 10 according to the present invention. This implant 10 has been mounted over the maxillary bone of a patient underneath the gum tissue 20 as shown in FIG. 7. As shown better in FIG. 2, the implant 10 includes a elongated thin base 12 which has been preformed into a shape generally corresponding to the bone in an edentuous span of a patient. Fenestration 14 penetrate the surface of the base 12. Toward the center of the base, there is threaded collar 16 which extends a few millimeters above the base. This threaded collar is adapted for receiving a similarly threaded post 18. Such a post is suitable for mounting an artificial tooth or acting as support for an artificial bridge.

Because the subperiosteal implant 10 has been prefabricated, it is not necessary to expose the patient's bone and to form a model of that bone from which the implant is made. Instead the implant is made of relatively pliable Titanium material which has the general shape of the bone. Once the implant 10 is located over the bone of the patient, it is gently tapped by blunt instruments, such as dental elevators, so that it conforms very closely to the shape of the bone. This has the effect of work hardening the material so that it tends to remain in the shape and to be securely mounted to the patient's bone.

The present invention is preferably used on the upper jaw bone, i.e. in maxillary unilateral sites, where the covering gum tissue is thicker and tougher than the mandible mucoperiosteal tissues. This maxillary tissue, when in a healed state, will sufficiently anchor the implant in place, especially when the tissue and blood vessels penetrate the fenestrations. Also the maxillary resorbed ridge, usually has more height then the resorbed mandible ridge and thus may provide a better surface to mold the implant to. Nevertheless, in appropriate circumstances, the technique can also be used along the mandible.

In installing the implant only a small incision 22 is made through the tissue. The tissue is then separated from the bone over a wider area by a tunneling procedure. Consequently, the subperiosteal implant, according to the present invention, can be installed with little or no trauma, and takes no more than 10 to 15 minutes to completely insert and suture it. Thus, the resulting surgery is far less expensive and painful than the prior procedures.

Figure 2:
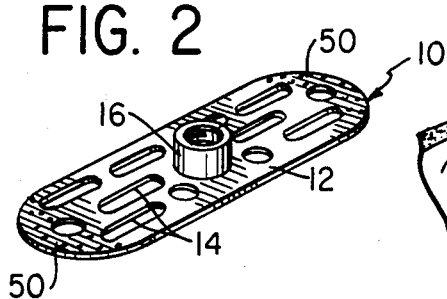
FIG. 2 is perspective view of a one-piece, prefabricated, subperiosteal implant according to the present invention.

The implant 10 of FIG. 2 is made of Titanium material which is a preferred material for surgical implantation. Previously subperiosteal implants were not made of Titanium because it is very difficult to cast Titanium. Therefore these implants were made of Vitallium (cobalt-chrome molybdium). This Vitallium material is very rigid, and unlike Titanium, cannot be molded or fashioned in areas where it might not fit the bone properly. Thus, the very complicated procedure of forming molds and casting material were used.

Figure 3:
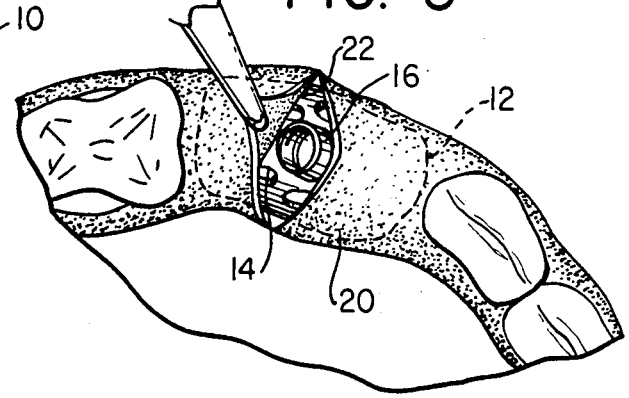
FIG. 3 is an occlusal plan view of the upper gum of a patient during the tunneling and insertion procedure for a subperiosteal implant according the present invention.

In FIG. 3 there is shown a plan view of the upper gum of a patient. In this figure, the insertion of the implant 10 beneath the gum tissue is illustrated. In particular, the dentist or oral surgeon will make a buccolingual incision 22 in the gum tissue. This incision will extend up one side of the bone ridge across the occlusal plane and down the other side. Then surgical instruments, e.g. properly sized periosteal elevators, are used to lift and separate the tissue on both sides of the incision 22. The incision 22 is made at the point where it is desired to have the post installed.

At least to one side of the incision, the tunneling is carried out to such an extent that the separated tissue extends for the length of a complete implant base 12. Typically the tissue is lifted distally for the entire length of the base portion. Mesially the tissues can be lifted a distance only one-half of the base portion. Then the implant itself is inserted into the incision, and slid distally beneath the separated tissue. The collar 16 is relatively low in height and thus can also be slipped under the separated tissue. When the implant has been moved completely under the tissue to one side of incision 22, the implant is completely resting on the bone. Then it can be moved back in the other or mesial direction so that the collar 16 is centered in the incision 22. Once in the proper place, various blunt instruments are used to mold the extremely thin base portion palatally, occlusally and buccally to conform exactly to the bone (see FIG. 7).

After the implant has been formed to the bone, the incision 22 is sutured. The sutures may leave the collar 16 exposed or may completely cover it. If conditions are proper, i.e., the implant is being held firmly in place, the collar 16 need not be covered. Instead a post 18 may be immediately installed, and an artificial tooth may then be cemented to post 18, or it may be used to support an artifical bridge.

After the suturing of incision 22, the fenestrations in base 12 allow the mucoperiosteal tissues to reattach to the bone through the base 12. Thus, in a preferred embodiment, the post 18 is not installed for several weeks or months to allow this reattachment to occur. This reattachment, of course, strengthens the securing of the subperiosteal implant in place. However, the post may be installed on the same day as the implant surgery and may be placed in function or allowed to remain exposed and out of function.

Figure 4:
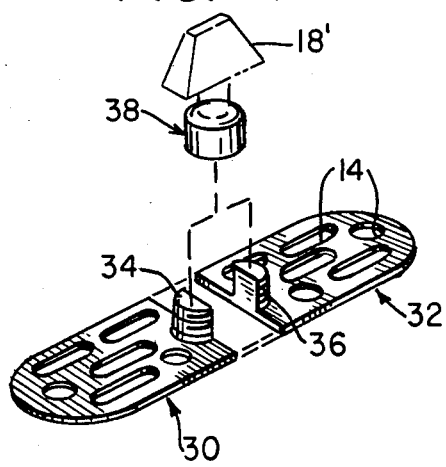
FIG. 4 is an exploded perspective view of a two-part subperiosteal implant with a connection cap according to the present invention.

In using the implant of FIG. 2, it was necessary to tunnel in one direction for a distance equal to the overall length of the elongated base 12. This additional surgical procedure can be reduced if an implant according to FIG. 4 is utilized. With the implant of FIG. 4, the structure of FIG. 2 is divided through the threaded collar 16. Of the two halves which form the implant of FIG. 4, the portion 32 has half of the base portion, with half of the collar 34 projecting from its mesial end. The second half 30 contains the other part of the base which contains the anterior portion of the flat fenestrated base and half of the collar 36 length protruding from its distal end. Naturally, the collar need not be divided strictly in half and need not be positioned in the center of the base 12.

Figure 5:
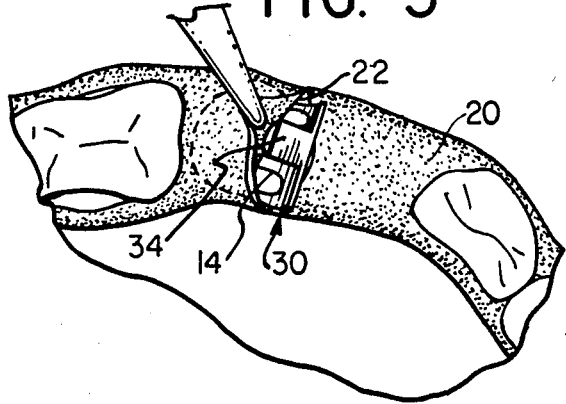
FIG. 5 is a plan view of the upper gum of a patient during insertion of one of the halves of a two-piece subperiosteal implant according to the present invention.

During the insertion procedure, the tissue is removed from the bone only for a distance equal to one-half of the overall implant base length to each side of the incision 22. First, one of the two portions of the implant is inserted in one direction under the tunneled tissue, and than the other portion is inserted in the other direction under the tissue as shown in FIG. 5. In order to hold the two halves 30, 32 of the implant together, the half collars 34, 36 on the respective parts have external threads which match and which may be engaged by an internally threaded cap 38. When cap 38 is screwed over portions 34, 36, the two halves are held together, and the molding of the plate portions 30, 32 to the bone of the patient can be carried out. Then the closing of the incision with sutures can be carried out.

In order to install a post on the divided implant, there are several alternatives available. As shown in dotted line FIG. 4, the post 18' may be integrally formed with cap 38 so that the post is installed at the time the cap is added to the base portions by screw threads or cement. As an alternative, a cap 40 may be provided with an aperture 39 as shown in FIG. 6 which allows access to the internal matching threads of the collar parts 34, 36. In this case, the portions 34, 36, when held together by cap 40, may receive a threaded post like post 18 as shown in FIG. 2.

As an additional alternative, if the threaded cap 40 leaves sufficient external threads on portions 34, 36 as shown in FIG. 6, the post and cap combination of FIG. 4 may engage these threads above cap 40. The locking caps 38, 40 can alternatively be secured to the half post 34, 36 by cement, as opposed to screw-threaded connections.

Prefabricated implants, according to the present invention, can be provided in various lengths, widths and configurations in order to accommodate the varying bone conditions the oral surgeon is likely to encounter. Besides the various shapes that the prefabricated implant may be made in, a shearing scissor may be used to change the shape to conform to a unique or atypical implant site.

Besides being useful for subperiosteal implants for fixed bridges, the present invention is also useful for removable bridges. As shown in FIG. 2, the base may be partially or totally covered with a ferrous, ferromagnetic or other magnetic mesh material 50 shown as a dotted area. This material is fastened to the base so that it is installed under the gum when the base is installed. Preferably such a magnetic implant would be provided at various locations along the gum line. Then, if a removable bridge is provided with a material that either attracts or is attracted by the material 50, the magnetic field which is created will help to hold the removable bridge in place. This will eliminate the need for the messy denture creams and adhesives presently used for this purpose.

While the invention has been particularly shown and described with reference to preferred embodiments thereof, it will be understood by those skilled in the art that various changes in form and details may be made therein without the departing from the spirit and scope of the invention.

I claim:
1. A prefabricated subperiosteal implant for supporting an artificial tooth structure, comprising:
   two thin elongated plates of pliable, work-hardenable material;
   short protrusions from the surface of each plate;
   means for fastening said two plates together such that the two plates are aligned and the short protrusions are adjacent one another; and
   a post for supporting an artificial tooth structure, said post being adapted for attachment to said short protrusions.
2. An implant as claimed in claim 1, wherein said short protrusion is an externally threaded cylinder and wherein said means for holding together is a threaded cap for screwing together the portions of the cylinder.
3. An implant as claimed in claim 2, wherein said cylinder also has internal threads and wherein said post has matching external threads such that said post may be mounted on the internal threads of said cylinder.

4. A prefabricated implant as claimed in claim 2, wherein the cap has an internal threaded aperture which is receivable on the external threads of the projecting cylinder.

5. A prefabricated subperiosteal implant for retaining an artificial removable full arch denture plate for a totally edentulous jawbone comprising;
   at least two thin elongated sheets of pliable work-hardenable material adapted to be positioned in respective spaced-apart locations along the edentulous jawbone beneath the periosteum and molded to the jawbone; and
   first and second magnetically susceptible materials at least partially covering said sheets and said denture plate, respectively, said second material being in the form of at least one magnet which is attracted to said first material in said sheets to hold the plate in place.

6. A method of inserting a subperiosteal implant on the dental bone ridge of a patient, comprising the steps of:
   making a lateral incision in the tissue covering the bone ridge, said incision extending across the bone ridge;
   tunneling the tissue such that it separates from the bone ridge both mesially and distally from the incision, the mesial and distal distance of the tunneled tissue being equal to the respective lengths of a two-part prefabricated implant;
   sliding first one, then the other, of the two parts of the implant under the tissue in the respective mesial and distal directions;
   securing the two parts of the implant together;
   molding the implant to the bone under the tissue;
   suturing the incision; and
   subsequently installing a post on the prefabricated implant.

* * * * *